United States Patent [19]

Green

[11] Patent Number: 4,559,180

[45] Date of Patent: Dec. 17, 1985

[54] TRANSESTERIFICATION OF ESTERS

[75] Inventor: Michael J. Green, Hedon, England

[73] Assignee: BP Chemicals Limited, England

[21] Appl. No.: 551,863

[22] Filed: Nov. 15, 1983

[30] Foreign Application Priority Data

Nov. 26, 1982 [GB] United Kingdom ................ 8233765
Jan. 7, 1983 [GB] United Kingdom ................ 8300444

[51] Int. Cl.$^4$ .................... C07C 67/02; C07C 67/03; C07C 68/00
[52] U.S. Cl. .................................. 260/463; 560/103; 560/217; 560/234
[58] Field of Search ................ 260/463; 560/103, 217, 560/234

[56] References Cited

U.S. PATENT DOCUMENTS 4,216,298 8/1980 Schreckenberg et al. .......... 260/463

FOREIGN PATENT DOCUMENTS 955232 4/1964 United Kingdom .
1489736 10/1977 United Kingdom .

*Primary Examiner*—Donald G. Daus
*Assistant Examiner*—Stephen M. Kapner
*Attorney, Agent, or Firm*—Brooks, Haidt, Haffner & Delahunty

[57] ABSTRACT

A process for the transesterification of a carboxylic or carbonic acid ester comprises reacting the carboxylic or carbonic acid ester under transesterification conditions with an alcohol in the presence, as catalyst, of either (i) a Group V element-containing Lewis base and an epoxide or (ii) a cyclic amidine.

The Lewis base can be an organic compound containing trivalent phosphorus or nitrogen and can be an amine, for example an amidine.

The process can be operated in the liquid phase at a temperature of from 15° to 150° C., and the catalyst is employed in solution.

Preferred catalysts are those where the cyclic amidine forms part of a fused ring system containing six and five membered rings, six and seven membered rings or two six membered rings.

15 Claims, No Drawings

TRANSESTERIFICATION OF ESTERS

This invention relates to a process for the transesterification of carboxylic acid and carbonic acid esters.

Esters, for example methyl acetate, methyl propionate and ethyl acetate are useful chemicals in industry and have wide application as industrial solvents. The preparation of an ester from another by reaction with an alcohol is called transesterification and is well known. Previously described transesterification catalysts include alkali metal alkoxides, organic titanates and metal carboxylates.

The transesterification of cyclic carbonates with an alcohol to form a dialkyl carbonate has been previously described in UK Pat. No. 1,489,736 using an organic Lewis base as a catalyst. As examples of organic Lewis bases are mentioned tertiary aliphatic amines such as tributyl amine and polymers containing tertiary aliphatic amine groups. However, no mention is made of cyclic amidines or guanidines, the use of which forms the subject of the present invention.

Further, the use of guanidines as catalysts has been previously described in UK Pat. No. 955,232 to effect transesterification of a terephthalate ester with a glycol to form a macromolecular polymethylene terephthalate.

It has now been found that (i) the presence of an epoxide will accelerate the transesterification catalysed by an amidine and that, not only amidines, but all Group V element-containing Lewis bases can be promoted in this way and (ii) cyclic amidines including guanidines are more effective catalysts than the non cyclic guanidines described in the above mentioned UK Pat. No. 955,232.

According to the present invention a process for the transesterification of a carboxylic acid or carbonic acid ester comprises reacting the carboxylic acid or carbonic acid ester under transesterification conditions with an alcohol in the presence, as catalyst, of either (i) a Group V element-containing Lewis base and an epoxide or (ii) a cyclic amidine.

The carboxylic acid ester starting material can be an alkyl, aryl, aralkyl or alkaryl ester of a saturated or unsaturated aliphatic or aromatic carboxylic acid. The carbonic acid ester starting material can be an alkyl, aralkyl (or a divalent group corresponding to these e.g. alkylene) ester of carbonic acid.

Conveniently the ester is a $C_1$ to $C_{12}$ alkyl, or, in the case of carbonic acid, $C_2$–$C_{12}$ alkylene ester.

Conveniently the alcohol is a $C_1$ to $C_{12}$ alkanol. The alcohol can be a primary alcohol. Glycols such as ethylene glycol and polyols can be used.

Unless the context clearly requires otherwise, the terms alkyl and aryl in the present specification are intended to include aralkyl (for example benzyl) and alkaryl respectively.

By Group V is meant the group of elements comprising nitrogen, phosphorus, arsenic, antimony and bismuth.

Conveniently the Lewis base is an organic compound containing trivalent phosphorus or trivalent nitrogen, for example of formula $R_3X$ where X is nitrogen or phosphorus and R is hydrogen or a monovalent organic group containing up to 12 carbon atoms. The R groups can be the same or different.

In the case of nitrogen the Lewis base can be an amine for example a primary, secondary or tertiary aliphatic or aromatic amine.

The Lewis base can be an amidine. When the Lewis base is a cyclic amidine it is not essential to employ an epoxide, although the epoxide will promote the action of the amidine.

By the term amidine is meant the grouping:

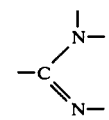

Conveniently the free valencies on the nitrogen atoms are attached to carbon atoms or hydrogen and the free valency on the carbon atom to another carbon atom or nitrogen atom. In the last mentioned case the structure will comprise a guanidine grouping.

The terms amidine and guanidine are therefore not mutually exclusive but in a genus and species relationship.

When an epoxide is present the amidine group-containing compound can be cyclic or acyclic. By cyclic amidine is meant that at least one of the nitrogen atoms of the above structure is in a ring. Preferably both the nitrogen atoms are in rings, which can be the same ring or different rings. Conveniently all three atoms of the above structure are present in one or more rings. The amidine group can form part of a fused ring system. For example the amidine can be 1,5-diazabicyclo[4.3.0]non-5-ene or 1,8 diazabicyclo[5.4.0]undec-7-ene, or 1,5,7-triazabicyclo[4.4.0]dec-5-ene.

In the case of an acyclic guanidine it is preferred that the nitrogen atoms bear substituents of carbon number two or more.

Suitable trivalent phosphorus-containing compounds are trialkyl and triaryl phosphines which can optionally contain more than one phosphorus atom.

The epoxide can be a 1:2 alkylene oxide such as ethylene oxide, 1:2 propylene oxide, 1:2 butylene oxide and the like.

Conveniently the molar proportions of Lewis base to epoxide are from 1:10 to 20:1, preferably 1:10 to 1:1.

Convenient molar proportions of alcohol to ester starting material are from 1:10 to 10:1.

As stated above, when an epoxide is not present it is essential that the amidine is cyclic. In this case the amidine can be any of those cyclic compounds mentioned above.

The reaction can be conviently effected at a temperature in the range 15° to 150° C. and a pressure for example from 1 bar to 150 bar.

Although the process can be carried out at room temperature eg 20° C. and atmospheric pressure it can be effected at higher temperatures with continuous removal, by distillation of one of the products.

The invention is illustrated by the following Examples.

In all the Examples, the reactants and products were in the liquid phase and the catalysts were employed in solution.

Examples 1 to 10 illustrate the use of a cyclic amidine and Examples 11 to 25 illustrate the use of epoxide to promote various Lewis bases.

EXAMPLE 1

Ethyl acetate to methyl acetate using a cyclic guanidine

Ethyl acetate (2 g) was added to a solution containing 2 g of methanol and 0.013 g of 1,5,7-triazabicyclo[4.4.0]-dec-5-ene (TBD) and the resulting mixture was maintained at 24° C. for 1 hour. Analysis of the liquid product by gas chromatography showed an ethyl acetate conversion of 76% to methyl acetate.

EXAMPLE 2

Ethyl formate to methyl formate

Example 1 was repeated except that 2 g of ethyl formate was used in place of ethyl acetate. Analysis of the liquid product showed an ethyl formate conversion of 77% to methyl formate.

EXAMPLE 3

Ethyl propionate to methyl propionate

Example 1 was repeated except that 2 g of ethyl propionate was used in place of ethyl acetate. After 2 hours, analysis of the liquid product showed an ethyl propionate conversion of 79% to methyl propionate.

EXAMPLE 4

Methyl acetate to ethyl acetate

Methyl acetate (2 g) was added to a solution containing 2 g of ethanol and 0.013 g of TBD and the resulting mixture was maintained at 24° C. for one hour. Analysis of the liquid product showed a methyl acetate conversion of 54% to ethyl acetate.

EXAMPLE 5

Methyl methacrylate to ethyl methacrylate

Example 4 was repeated except that 2 g of methyl methacrylate was used in place of methyl acetate. Analysis of the liquid product showed a methyl methacrylate conversion of 34% to ethyl methacrylate.

EXAMPLE 6

Methyl acrylate to ethyl acrylate

Example 4 was repeated except that 2 g of methyl acrylate was used in place of methyl acetate and the reaction time was increased to 2 hours. Analysis of the liquid product showed a methyl acrylate conversion of 24% to ethyl acrylate.

EXAMPLE 7

Benzyl acetate to methyl acetate

Benzyl acetate (2 g) was added to a solution containing 2 g of methanol and 0.039 g of TBD. The resulting solution was maintained at 24° C. for 2 hours. Analysis of the product showed a benzyl acetate conversion of 92% to methyl acetate.

EXAMPLE 8

Ethyl acetate to methyl acetate using a cyclic amidine

Example 1 was repeated except that 0.075 g of 1,5-diazabicyclo[4.3.0]-non-5-ene (DBN) was used as a catalyst in place of TBD, and the reaction time was increased to 2 hours. Analysis of the liquid product showed an ethyl acetate conversion of 37% to methyl acetate.

EXAMPLE 9

Ethyl acetate to methyl acetate using a cyclic amidine

Example 8 was repeated except that 0.07 g of 1,8-diazabicyclo[5.4.0]undec-7-ene was used as a catalyst in place of DBN. Analysis of the liquid product showed an ethyl acetate conversion of 52% to methyl acetate.

COMPARATIVE EXAMPLE A

Ethyl acetate to methyl acetate using an acyclic guanidine

Example 1 was repeated except that 0.07 g of N,N,N'N'-tetramethylguanidine was used as a catalyst in place of TBD. Analysis of the liquid product showed an ethyl acetate conversion of 35% to methyl acetate.

EXAMPLE 10

Ethyl benzoate to methyl benzoate

Ethyl benzoate (2 g) was added to a solution containing 2 g of methanol and 0.048 g of TBD and the resulting solution was maintained at 24° C. for 2 hours. Analysis of the liquid product showed an ethyl benzoate conversion of 86% to methyl benzoate.

COMPARATIVE EXAMPLE B

Starting material:ethyl acetate

Example 1 was repeated in the absence of TBD. Analysis of the liquid product indicated that no reaction had occurred.

COMPARATIVE EXAMPLE C

Starting material:ethyl acetate

Example 1 was repeated except that 0.08 g of triethylamine was used as a catalyst in place of TBD. Analysis of the liquid product indicated that no reaction had occurred.

EXAMPLE 11

Epoxide promoted cyclic amidine

Ethyl acetate (2 g) was added to a solution containing 2 g of methanol, 0.073 g of 1,5-diazabicyclo[4.3.0]non-5-ene (DBN), and 0.11 g of 1:2 propylene oxide, and the resulting mixture was maintained at 24° C. for 2 h. Analysis of the liquid product by gas chromatography showed an ethyl acetate conversion of 76% to methyl acetate.

EXAMPLE 12

Example 11 was repeated in the absence of 1:2 propylene oxide. Analysis of the liquid product showed an ethyl acetate conversion of 37% to methyl acetate.

Examples 13–16 illustrate the effect of varying the epoxide concentration with a cyclic amidine

EXAMPLE 13

A solution containing 2 g of methanol, 0.0075 g of DBN, and 0.0035 g of 1:2 propylene oxide was allowed to stand for 90 h at room temperature after which time 2 g of ethyl acetate was added, and the resulting mixture was maintained at 24° C. for 2 h. Analysis of the liquid product showed an ethyl acetate conversion of 47% to methyl acetate.

EXAMPLE 14

Example 13 was repeated in the presence of 0.0070 g of 1:2 propylene oxide. Analysis of the liquid product showed an ethyl acetate conversion of 58% to methyl acetate.

EXAMPLE 15

Example 13 was repeated in the presence of 0.0175 g of 1:2 propylene oxide. Analysis of the liquid product showed an ethyl acetate conversion of 65% to methyl acetate.

EXAMPLE 16

Example 13 was repeated in the presence of 0.035 g of 1:2 propylene oxide. Analysis of the liquid product showed an ethyl acetate conversion of 71% to methyl acetate.

EXAMPLE 17

Example 13 was repeated in the absence of 1:2 propylene oxide. Analysis of the liquid product after 3½ h showed an ethyl acetate conversion of only 14% to methyl acetate.

EXAMPLE 18

Example 15 was repeated except that the mixture of methanol, DBN, and 1:2 propylene oxide was allowed to stand for 140 h, and 2 g of ethyl formate was used in place of ethyl acetate. Analysis of the liquid product after 1½ h showed an ethyl formate conversion of 78% to methyl formate.

EXAMPLE 19

A solution containing 10 g of methanol, 1.75 g of 1:2 propene oxide, and 6.05 g of tributylphosphine was heated to 100° C. in a sealed Fischer-Porter tube under an initial nitrogen pressure of 50 psi. On cooling, the solution was diluted 50 fold with methanol and 2.1 g of the resulting solution was added to 2 g of ethyl acetate.

Analysis of the liquid product after 2 h showed an ethyl acetate conversion of 79% to methyl acetate.

COMPARATIVE EXAMPLE D

Example 19 was repeated in the absence of 1:2 propylene oxide. Analysis of the liquid product indicated that no reaction had occurred.

EXAMPLE 20

Example 19 was repeated except that 2 g of benzyl acetate was used in place of ethyl acetate. Analysis of the liquid product showed a benzyl acetate conversion of 91% to methyl acetate.

EXAMPLE 21

Example 19 was repeated except that 3.05 g of triethylamine was used in place of tributylphosphine. Analysis of the liquid product showed an ethyl acetate conversion of 63% to methyl acetate.

EXAMPLE 22

Example 21 was repeated except that 2 g of benzyl acetate was used in place of ethyl acetate. Analysis of the liquid product showed a benzyl acetate conversion of 83% to methyl acetate.

EXAMPLE 23

Example 19 was repeated except that 2.35 g of pyridine was used in place of tributylphosphine. Analysis of the liquid product showed an ethyl acetate conversion of 50% to methyl acetate.

EXAMPLE 24

Propylene carbonate to dimethyl carbonate

Propylene carbonate (1 g) was added to a solution containing 1 g of methanol, 0.05 g of DBN, and 0.095 g of 1:2 propylene oxide and the resulting mixture was maintained at 24° C. for 10 min. Analysis of the liquid product showed a propene carbonate conversion of 40% to dimethyl carbonate.

EXAMPLE 25

Example 24 was repeated in the absence of 1:2 propylene oxide. Analysis of the liquid product showed a propylene carbonate conversion of 11% to dimethyl carbonate.

In the above examples the abbreviations g, h and psi refer to grams, hours and pounds per square inch respectively.

I claim:

1. A process for the transesterification of a carboxylic acid ester or carbonic acid ester which process comprises reacting the carboxylic acid ester or the carbonic acid ester under transesterification conditions with an alcohol in the presence, as catalyst, of
    (A) a Lewis base containing an element selected from the group consisting of nitrogen, phosphorus, arsenic, antimony and bismuth and
    (B) an epoxide.

2. A process as claimed in claim 1 wherein the Lewis base is an organic compound containing trivalent phosphorus or nitrogen.

3. A process as claimed in claim 2 wherein the Lewis base is an amine.

4. A process as claimed in claim 3 wherein the amine is an amidine.

5. A process as claimed in claim 1 wherein the temperature is from 15° to 150° C.

6. A process as claimed in claim 1 for the production of a dialkyl carbonate which process comprises reacting an alkylene carbonate with an alkanol.

7. A process as claimed in claim 1, wherein the Lewis base is an organic compound of formula $R_3X$,
    where X is nitrogen or phosphorus, and R is hydrogen or a monovalent organic group containing up to 12 carbon atoms, wherein the R groups can be the same or different.

8. A process as claimed in claim 1, wherein the Lewis base is selected from the group consisting of tributylphosphine, triethylamine, and pyridine.

9. A process as claimed in claim 1, wherein the epoxide is selected from the group consisting of ethylene oxide, 1:2-propylene oxide and 1:2-butylene oxide.

10. A process as claimed in claim 1, wherein the molar proportions of Lewis base to epoxide are from 1:10 to 20:1.

11. A process as claimed in claim 1, wherein the molar proportions of Lewis base to epoxide are from 1:10 to 1:1.

12. A process as claimed in claim 1, wherein the molar proportions of alcohol to ester starting material are from 1:10 to 10:1.

13. A process as claimed in claim 1, wherein the carboxylic acid ester is selected from the group consisting of ethyl acetate, ethyl formate, ethyl propionate, methyl acetate, methyl methacrylate, methyl acrylate, benzyl acetate and ethyl benzoate.

14. A process as claimed in claim 1, wherein the alcohol is selected from the group consisting of a $C_1$ to $C_{12}$ alkanol, and ethylene glycol.

15. A process as claimed in claim 1, wherein the alcohol is selected from the group consisting of methanol and ethanol.

* * * * *